US 6,743,179 B2

(12) United States Patent
Narimatsu et al.

(10) Patent No.: US 6,743,179 B2
(45) Date of Patent: *Jun. 1, 2004

(54) ARTERIOSTENOSIS INSPECTING APPARATUS

(75) Inventors: Kiyoyuki Narimatsu, Komaki (JP); Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/407,191

(22) Filed: Apr. 7, 2003

(65) Prior Publication Data

US 2004/0059231 A1 Mar. 25, 2004

(30) Foreign Application Priority Data

Sep. 19, 2002 (JP) .......................... 2002-273913

(51) Int. Cl.[7] .................................. A61B 5/00
(52) U.S. Cl. ................... 600/485; 600/492; 600/490; 600/494
(58) Field of Search ................. 600/485, 490, 600/493–6, 500, 492

(56) References Cited

U.S. PATENT DOCUMENTS

| 5,048,533 A | * | 9/1991 | Muz | 600/492 |
| 5,050,613 A | * | 9/1991 | Newman et al. | 600/483 |
| 5,152,296 A | * | 10/1992 | Simons | 600/483 |
| 5,289,823 A | * | 3/1994 | Eckerle | 600/492 |
| 5,724,980 A | * | 3/1998 | Nakamura et al. | 600/492 |
| 5,743,857 A | * | 4/1998 | Shinoda et al. | 600/496 |
| 6,355,000 B1 | | 3/2002 | Ogura | |
| 6,524,257 B2 | * | 2/2003 | Ogura | 600/490 |

FOREIGN PATENT DOCUMENTS

| EP | 1 050 266 A1 | 5/2000 | |
| EP | 1 050 267 A1 | 5/2000 | |
| EP | 1 050 268 A1 | 5/2000 | |
| EP | 1 053 714 A3 | 5/2000 | |
| EP | 1 053 714 A2 | 5/2000 | |
| EP | 1 240 866 A1 | 11/2001 | |
| JP | 5-176900 | * 7/1993 | 600/492 |
| JP | B2 3140007 | 12/2000 | |

* cited by examiner

*Primary Examiner*—Robert L. Nasser
(74) *Attorney, Agent, or Firm*—Oliff & Berridge, PLC

(57) ABSTRACT

An arteriostenosis inspecting apparatus including a left-superior-limb-blood-pressure measuring device which measures a left-superior-limb blood pressure of a left superior limb of a living subject, a right-superior-limb-blood-pressure measuring device which measures a right-superior-limb blood pressure of a right superior limb of the subject, and a left-and-right-superior-limb-blood-pressure-ratio determining device which determines a left-and-right-superior-limb blood-pressure ratio as a ratio of one of the left-superior-limb blood pressure and the right-superior-limb blood pressure to the other.

6 Claims, 3 Drawing Sheets

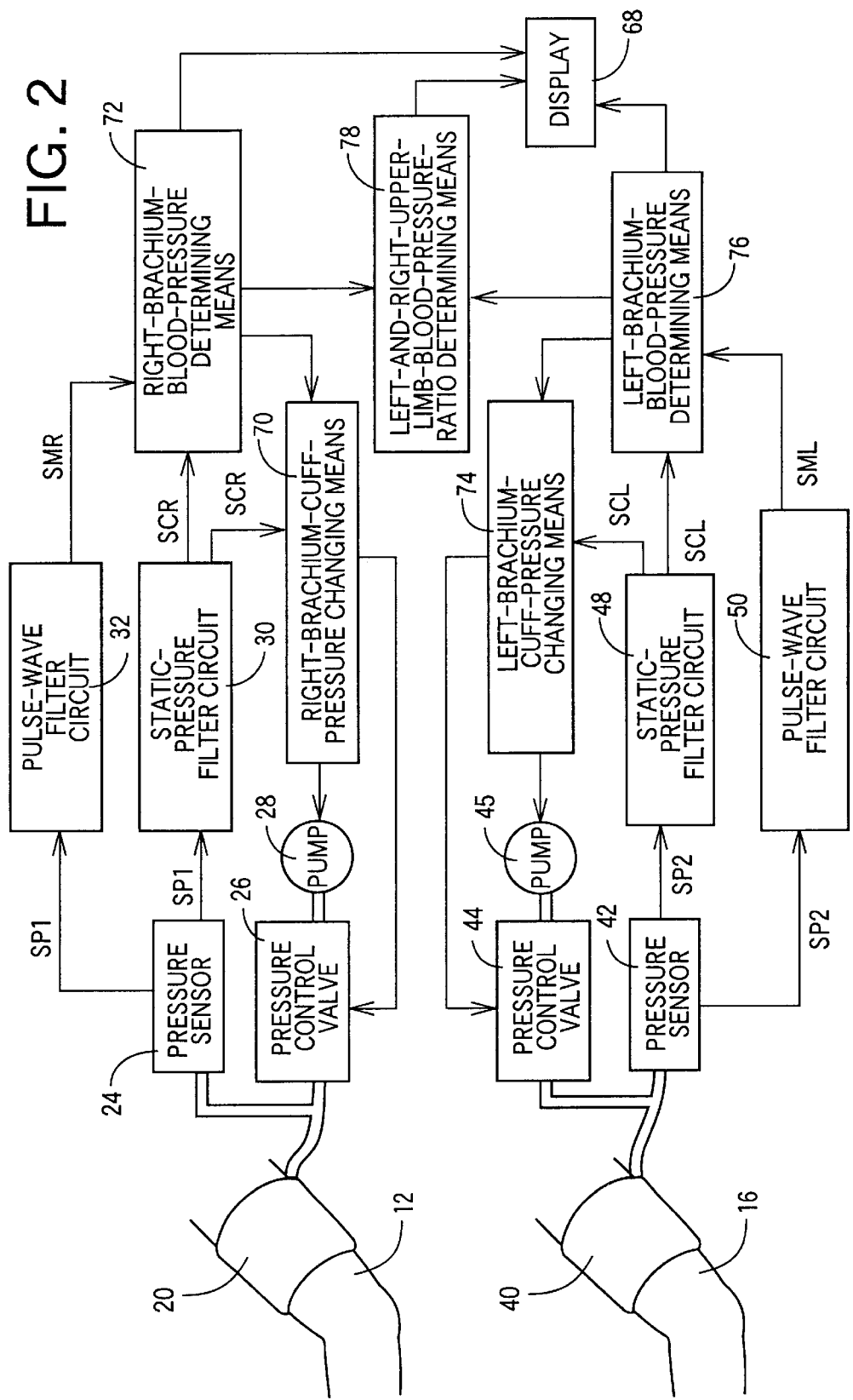

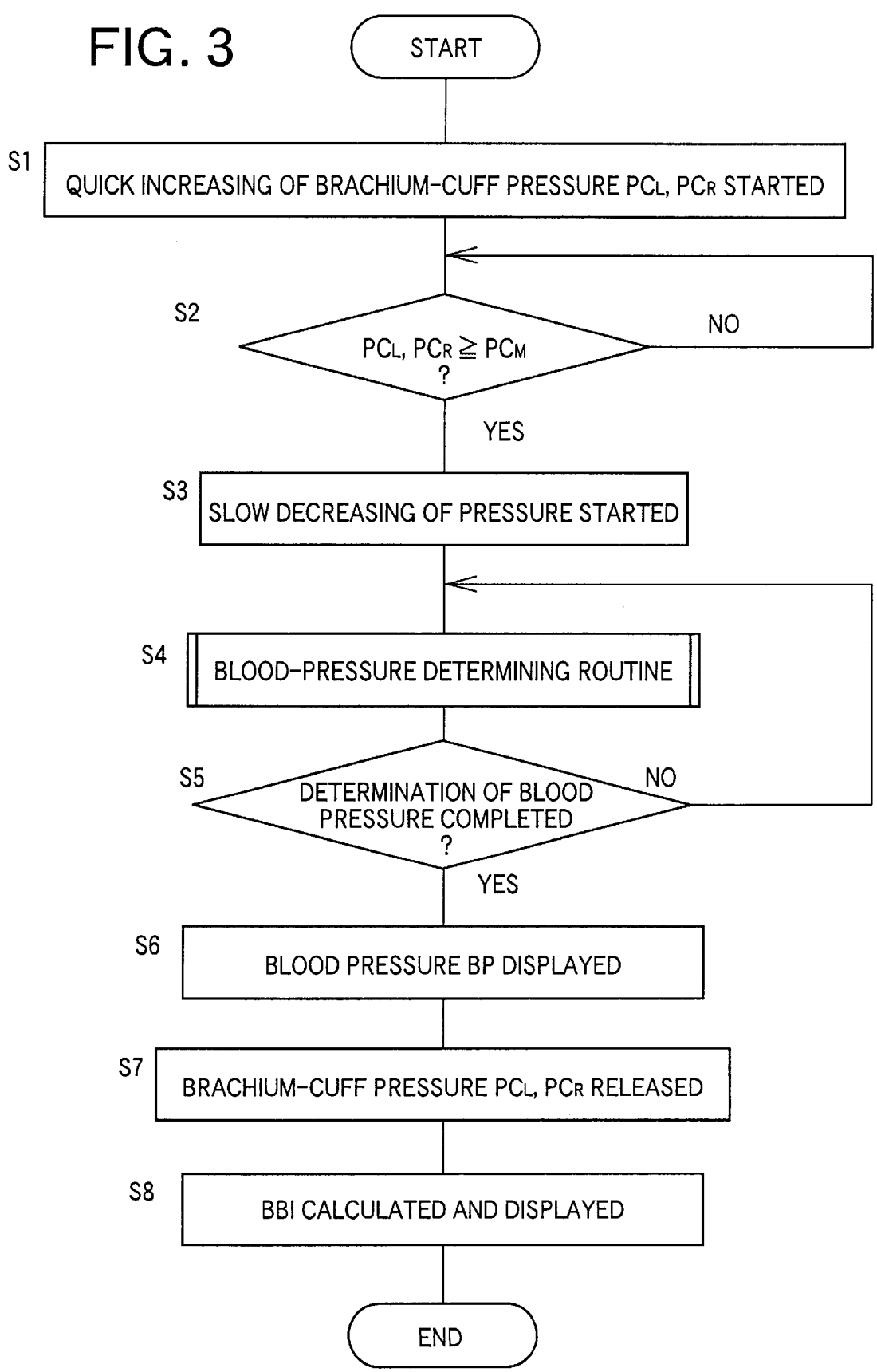

ARTERIOSTENOSIS INSPECTING APPARATUS

BACKGROUND OF THE INVENTION

1. Field of the Invention

The present invention relates to an arteriostenosis inspecting apparatus for inspecting absence or presence of arteriostenosis of a superior-limb artery of a living subject. In the present application, the superior-limb artery is defined as encompassing a subclavian artery.

2. Related Art Statement

Atherosclerosis is a sort of arteriosclerosis and is characterized in that lipid, in particular, cholesterol deposits on the inner wall of artery and accordingly the arterial wall thickens. An artery suffering atherosclerosis has stenosis and its diameter reduces. Thus, atherosclerosis is also called arteriostenosis or arteriosclerosis obliterans.

As a device for inspecting arteriostenosis, there is known an ankle-and-brachium-blood-pressure-index measuring device that inspects the stenosis by utilizing a fact that blood pressure lowers on a downstream side of a stenotic portion of an artery. Japanese Patent No. 3140007 or its corresponding U.S. Pat. No. 6,355,000 discloses an example of the index measuring device. The disclosed device includes two cuffs that are adapted to be worn on an ankle and a brachium of a living subject so as to measure an ankle blood pressure and a brachium blood pressure of the subject, respectively, then calculates an ankle-and-brachium blood-pressure index as a ratio between the ankle blood pressure and the brachium blood pressure, and finally inspects presence or absence of arteriostenosis based on the thus calculated ankle-and-brachium blood-pressure index.

Generally, an ankle-and-brachium blood-pressure index is calculated as a proportion of an ankle systolic blood pressure to a brachium systolic blood pressure. In this case, if the thus calculated ankle-and-brachium blood-pressure index is smaller than 0.9, that is, if the ankle systolic blood pressure is smaller than the product of the brachium systolic blood pressure and 0.9, it can be judged that the subject is suspected of arteriostenosis.

In many cases arteriostenosis occurs to an inferior-limb artery, but in some cases it occurs to a superior-limb artery. For example, it is known that the stenosis occurs to a subclavian artery. However, as described above, ankle-and-brachium blood-pressure index is calculated as the proportion of ankle blood pressure to brachium blood pressure. That is, whether the ankle blood pressure is abnormal is judged by comparing the ankle blood pressure with the brachium blood pressure. Therefore, based on the ankle-and-brachium blood-pressure index, it can be judged whether an artery between the heart and the ankle, in particular, an inferior-limb artery has stenosis. However, it is difficult to judge, based on the ankle-and-brachium blood-pressure index, whether a superior-limb artery has stenosis.

SUMMARY OF THE INVENTION

It is therefore an object of the present invention to provide an arteriostenosis inspecting apparatus which can inspect presence or absence of stenosis of a superior-limb artery of a living subject.

The above object has been achieved by the present invention. According to the present invention, there is provided an arteriostenosis inspecting apparatus, comprising a left-superior-limb-blood-pressure measuring device which measures a left-superior-limb blood pressure of a left superior limb of a living subject; a right-superior-limb-blood-pressure measuring device which measures a right-superior-limb blood pressure of a right superior limb of the subject; and a left-and-right-superior-limb-blood-pressure-ratio determining means for determining a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device.

If one of left and right superior-limb arteries of the subject has stenosis, then the blood pressure in the one artery lowers. Therefore, a left-and-right-superior-limb blood-pressure ratio determined by the left-and-right-superior-limb-blood-pressure-ratio determining means in the case where neither of the left and right superior-limb arteries has stenosis differs from that determined in the case where either of the two superior-limb arteries has stenosis. Thus, based on the left-and-right-superior-limb blood-pressure ratio determined by the left-and-right-superior-limb-blood-pressure-ratio determining means, a person such as a doctor can diagnose presence or absence of arteriostenosis of a superior-limb artery such as a subclavian artery.

Here, preferably, the left-and-right-superior-limb-blood-pressure-ratio determining means determines the left-and-right-superior-limb blood-pressure ratio by using a lower one of the left-superior-limb blood pressure and the right-superior-limb blood pressure as a numerator of the ratio and using a higher one of the left-superior-limb blood pressure and the right-superior-limb blood pressure as a denominator of the ratio. According to this feature, the presence of arteriostenosis always results in lowering the left-and-right-superior-limb blood-pressure ratio. Thus, when the subject suffers arteriostenosis, the left-and-right-superior-limb blood-pressure ratio changes in the same manner as the ankle-and-brachium blood-pressure index as another index useful in diagnosing arteriostenosis. Therefore, misdiagnoses can be reduced.

Also, preferably, the left-and-right-superior-limb-blood-pressure-ratio determining means determines the left-and-right-superior-limb blood-pressure ratio by using a preselected one of the left-superior-limb blood pressure and the right-superior-limb blood pressure as a denominator of the ratio. In this case, the person can judge which one of the left and right superior limbs has arteriostenosis, depending upon whether the left-and-right-superior-limb blood-pressure ratio is greater or smaller than 1.

BRIEF DESCRIPTION OF THE DRAWINGS

The above and optional objects, features, and advantages of the present invention will be better understood by reading the following detailed description of preferred embodiments of the invention when considered in conjunction with the drawings, in which:

FIG. 2 is a diagrammatic view for explaining essential control functions of an electronic control device of the arteriostenosis inspecting apparatus of FIG. 1; and FIG. 3 is a flow chart representing the essential control functions of the electronic control device, shown in the diagrammatic view of FIG. 2.

DETAILED DESCRIPTION OF PREFERRED EMBODIMENTS

Figure 1:
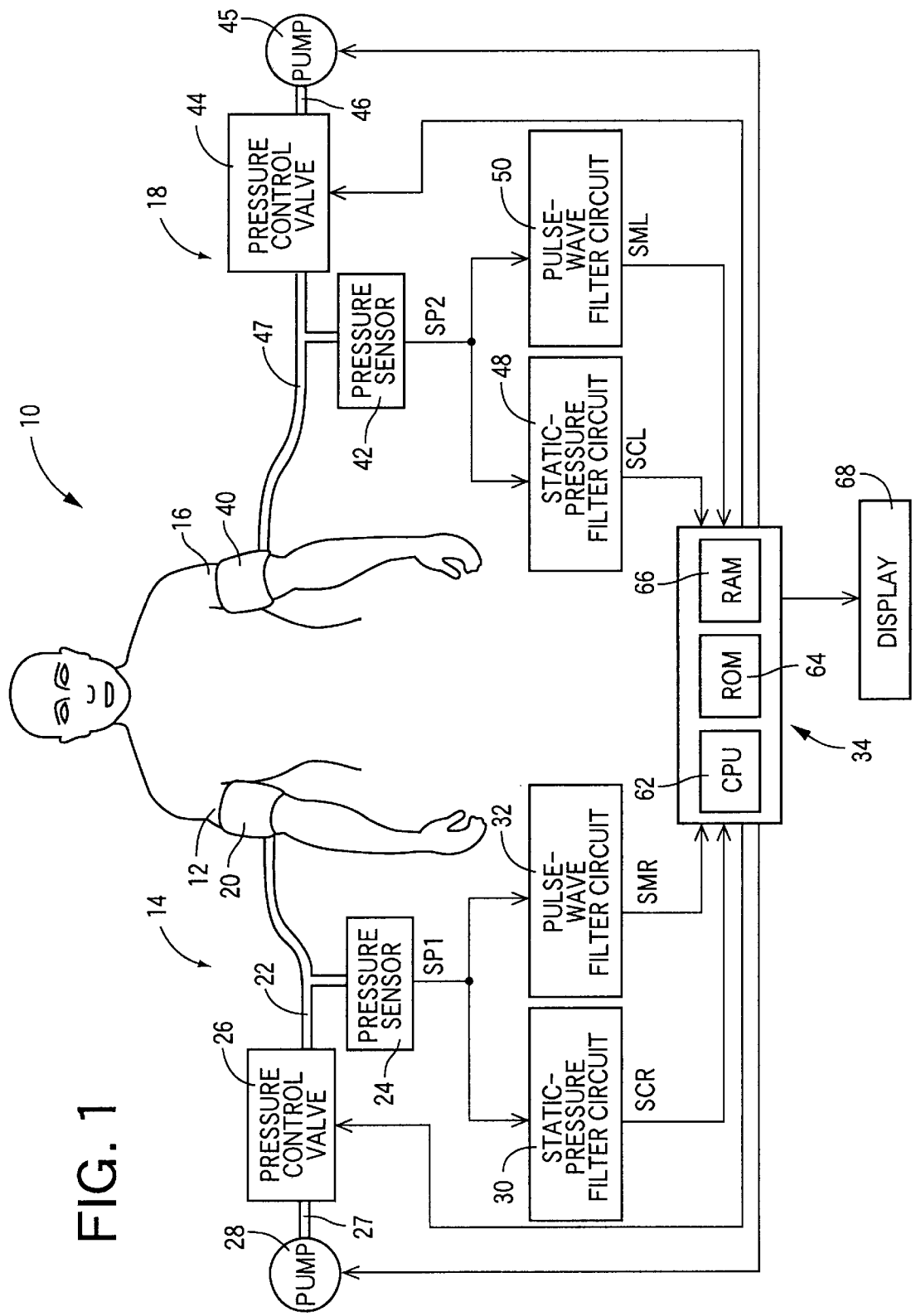
FIG. 1 is a diagrammatic view for explaining a construction of an arteriostenosis inspecting apparatus to which the present invention is applied.

Hereinafter, there will be described a preferred embodiment of the present invention in detail by reference to the drawings. FIG. 1 shows a view for explaining a construction of an arteriostenosis inspecting apparatus 10 to which the present invention is applied.

The arteriostenosis inspecting apparatus 10 includes a right-brachium-blood-pressure measuring device 14 which measures a blood pressure of a right brachium 12 of a living subject and functions as a right-superior-limb-blood-pressure measuring device; and a left-brachium-blood-pressure measuring device 18 which measures a blood pressure of a left brachium 16 of the subject and functions as a left-superior-limb-blood-pressure measuring device.

The right-brachium-blood-pressure measuring device 14 includes a cuff 20 which includes a belt-like cloth bag and a rubber bag accommodated in the cloth bag and which is adapted to be worn on the right brachium 12. The cuff 20 is connected via a piping 22 to a pressure sensor 24 and a pressure control valve 26. The pressure control valve 26 is connected via a piping 27 to an air pump 28. The pressure sensor 24 supplies a first pressure signal SP1 to a static-pressure filter circuit 30 and a pulse-wave filter circuit 32. The measuring device 14 additionally includes an electronic control device 34.

The pressure control valve 26 adjusts a pressure of a pressurized air supplied from the air pump 28, and supplies the pressure-adjusted air to the cuff 20, or discharges the pressurized air from the cuff 20, so as to control an air pressure in the cuff 20.

The pressure sensor 24 detects the air pressure in the cuff 20, and supplies the first pressure signal SP1 representing the detected air pressure, to each of the static-pressure filter circuit 30 and the pulse-wave filter circuit 32. The static-pressure filter circuit 30 includes a low-pass filter which extracts, from the first pressure signal SP1, a right-brachium cuff-pressure signal $SC_R$ representing a static component of the detected air pressure, i.e., a pressing pressure of the cuff 20 (hereinafter, referred to as the right-brachium cuff pressure $PC_R$). The filter circuit 30 supplies the right-brachium cuff-pressure signal $SC_R$ to the electronic control device 34 via an A/D (analog-to-digital) converter, not shown.

The pulse-wave filter circuit 32 includes a band-pass filter which extracts, from the first pressure signal SP1, a right-brachium pulse-wave signal $SM_R$ representing an oscillatory component of the detected air pressure that has specific frequencies. The filter circuit 32 supplies the right-brachium pulse-wave signal $SM_R$ to the electronic control device 32 via an A/D converter, not shown. The right-brachium pulse-wave signal $SM_R$ represents a right-brachium pulse wave as a pressure oscillation that is transmitted from a right brachial artery of the subject to the cuff 20.

The left-brachium-blood-pressure measuring device 18 includes a cuff 40, a pressure sensor 42, a pressure control valve 44, an air pump 45, a static-pressure filter circuit 48, and a pulse-wave filter circuit 50 that have respective arrangements identical with those of the counterparts 20, 24, 26, 28, 30, 32 of the above-described right-brachium-blood-pressure measuring device 14; and additionally includes the electronic control device 34.

The cuff 40 is adapted to be worn on the left brachium 16. The pressure control valve 44 and the air pump 45 are connected to each other via a piping 46; and the cuff 40, the pressure sensor 42, and the pressure control valve 44 are connected to each other via a piping 47. The pressure sensor 42 supplies a second pressure signal SP1 representing an air pressure in the cuff 40, to each of the static-pressure filter circuit 48 and the pulse-wave filter circuit 50. The static-pressure filter circuit 48 extracts, from the second pressure signal SP2, a left-brachium cuff-pressure signal $SC_L$ representing a static component of the detected air pressure, i.e., a pressing pressure of the cuff 40 (hereinafter, referred to as the left-brachium cuff pressure $PC_L$). The filter circuit 48 supplies the left-brachium cuff-pressure signal $SC_L$ to the electronic control device 34 via an A/D converter, not shown. The pulse-wave filter circuit 50 extracts, from the second pressure signal SP2, a left-brachium pulse-wave signal $SM_L$ representing an oscillatory component of the detected air pressure that has specific frequencies. The filter circuit 50 supplies the left-brachium pulse-wave signal $SM_L$ to the electronic control device 34 via an A/D converter, not shown. The left-brachium pulse-wave signal $SM_L$ represents a left-brachium pulse wave as a pressure oscillation that is transmitted from a left brachial artery of the subject to the cuff 40.

The electronic control device 34 is provided by a so-called microcomputer including a CPU (central processing unit) 62, a ROM (read only memory) 64, a RAM (random access memory) 66, and an I/O (input-and-output) port, not shown. The CPU 62 processes signals according to control programs pre-stored in the ROM 64, while utilizing a temporary-storage function of the RAM 66. The CPU 62 outputs, from the I/O port, drive signals to the air pumps 28, 45 and the pressure control valves 26, 44, so as to control the respective air pressures in the cuffs 20, 40. In addition, the CPU 62 processes the signals supplied to the control device 34, so as to determine left-brachium blood-pressure values BPL and right-brachium blood-pressure values BPR, and operates a display device 68 to display the thus determined left-brachium and right-brachium blood-pressure values BPL, BPR. In addition, the CPU 62 calculates, based on the left-brachium and right-brachium blood-pressure values BPL, BPR, a left-and-right-superior-limb blood-pressure ratio BBI, and operates the display device 68 to additionally display the thus calculated blood-pressure ratio BBI. The display device 68 may be a CRT (cathode ray tube) or a printer.

FIG. 2 is a diagrammatic view for explaining essential control functions of the electronic control device 34. A right-brachium-cuff-pressure changing device or means 70 controls, according to a command signal supplied from a right-brachium-blood-pressure determining device or means 72, described below, and based on the right-brachium-cuff-pressure signal $SC_R$ supplied from the static-pressure filter circuit 30, the air pump 28 and the pressure control valve 26 connected to the same 28, so as to change the right-brachium cuff pressure $PC_R$, as follows: First, the right-brachium cuff pressure $PC_R$ is quickly increased up to a prescribed target pressure value $PC_M$ (e.g., 180 mmHg) that would be higher than a systolic blood pressure $PBR_{SYS}$ of the right brachium 12, and then the right-brachium cuff pressure $PC_R$ is slowly decreased at a rate of about 3 mmHg/sec. After a right-brachium diastolic blood pressure $BPR_{DIA}$ is determined, the right-brachium cuff pressures $PC_R$ is released to an atmospheric pressure.

The right-brachium-blood-pressure determining means 72 determines the change of the right-brachium cuff pressure $PC_R$ represented by the right-brachium-cuff-pressure signal $SC_R$ continuously supplied from the static-pressure filter circuit 30 during the slow decreasing of the right-brachium cuff pressure $PC_R$ under the control of the right-brachium-cuff pressure changing means 70, and the change of respective amplitudes of successive heartbeat-synchronous pulses of the right-brachium pulse wave represented by the right-brachium-pulse-wave signal $SM_R$ continuously supplied from the pulse-wave filter circuit 32 during the slow decreasing of the right-brachium cuff pressure $PC_R$. Then, based on the thus determined changes of the right-brachium cuff pressure $PC_R$ and the respective amplitudes of successive pulses of the right-brachium pulse wave, the determining means 72 determines blood-pressure values of the right brachium 12, i.e., a right-brachium systolic blood pressure $BPR_{SYS}$, a right-brachium diastolic blood pressure $BPR_{DIA}$, and a right-brachium mean blood pressure $BPR_{MEAN}$, according to a well-known oscillometric algorithm. In addition, the determining means 72 operates the display device 68 to display the thus determined right-brachium blood-pressure values BPR.

A left-brachium-cuff-pressure changing device or means 74 controls, according to a command signal supplied from a left-brachium-blood-pressure determining device or means 76, described below, and based on the left-brachium-cuff-pressure signal $SC_L$ supplied from the static-pressure filter circuit 48, the air pump 45 and the pressure control valve 44 connected to the same 45, so as to change the left-brachium cuff pressure $PC_L$ in the same manner as the manner in which the right-brachium-cuff-pressure changing means 70 changes the right-brachium cuff pressure $PC_R$. That is, first, the left-brachium cuff pressure $PC_L$ is quickly increased up to the above-described target pressure value $PC_M$, and then the left-brachium cuff pressure $PC_L$ is slowly decreased at the rate of about 3 mmHg/sec. After a left-brachium diastolic blood pressure $BPL_{DIA}$ is determined, the left-brachium cuff pressures $PC_L$ is released to an atmospheric pressure.

The left-brachium-blood-pressure determining means 76 determines the change of the left-brachium cuff pressure $PC_L$ represented by the left-brachium-cuff-pressure signal $SC_L$ continuously supplied from the static-pressure filter circuit 48 during the slow decreasing of the left-brachium cuff pressure $PC_L$ under the control of the left-brachium-cuff-pressure changing means 74, and the change of respective amplitudes of successive heartbeat-synchronous pulses of the left-brachium pulse wave represented by the left-brachium-pulse-wave signal $SM_L$ continuously supplied from the pulse-wave filter circuit 50 during the slow decreasing of the left-brachium cuff pressure $PC_L$. Then, based on the thus determined changes of the left-brachium cuff pressure $PC_L$ and the respective amplitudes of successive pulses of the left-brachium pulse wave, the determining means 76 determines blood-pressure values of the left brachium 16, i.e., a left-brachium systolic blood pressure $BPL_{SYS}$, a left-brachium diastolic blood pressure $BPL_{DIA}$, and a left-brachium mean blood pressure $BPL_{MEAN}$, according to the well-known oscillometric algorithm. In addition, the determining means 76 operates the display device 68 to display the thus determined left-brachium blood-pressure values BPL.

A left-and-right-superior-limb-blood-pressure-ratio calculating device or means 78 calculates a left-and-right-superior-limb blood-pressure ratio BBI as a ratio between the left-brachium blood pressure BPL determined by the left-brachium-blood-pressure determining means 76 and the right-brachium blood pressure BPR determined by the right-brachium-blood-pressure determining means 72. In addition, the calculating means 78 operates the display device 68 to display the thus calculated left-and-right-superior-limb blood-pressure ratio BBI. The left-and-right-superior-limb blood-pressure ratio BBI may be a ratio between the left and right systolic blood pressure $BBL_{SYS}$, $BBR_{SYS}$, a ratio between the left and right mean blood pressure $BBL_{MEAN}$, $BBR_{MEAN}$, or a ratio between the left and right diastolic blood pressure $BBL_{DIA}$, $BBR_{DIA}$, and the higher one of the left-brachium blood pressure BPL and the right-brachium blood pressure BPR is used as a denominator of the ratio BBI and the lower one is used as a numerator of the same BBI.

FIG. 3 shows a flow chart for explaining the essential control functions of the electronic control device 34, shown in the diagrammatic view of FIG. 2.

First, at Step S1 (hereinafter, "Step" is omitted), the control device operates the two air pumps 28, 45 and the two pressure control valves 26, 44 so as to start quick increasing of the right-brachium cuff pressure $PC_R$ and the left-brachium cuff pressure $PC_L$. Subsequently, at S2, the control device judges whether both of the right-brachium cuff pressure $PC_R$ and the left-brachium cuff pressure $PC_L$ have reached the prescribed target pressure value $PC_M$, e.g., 180 mmHg. If a negative judgment is made at S2, S2 is repeated On the other hand, if a positive judgment is made at S2, the control goes to S3 to stop the air pumps 28, 45 and operate the pressure control valves 26, 44 so as to start slow decreasing of the right-brachium cuff pressure $PC_R$ and the left-brachium cuff pressure $PC_L$ at the prescribed rate of about 3 mmHg/sec.

Then, the control goes to S4 through S6 corresponding to the right-brachium-blood-pressure determining means 72 and the left-brachium-blood-pressure determining means 76. First, at S4, the control device carries out a blood-pressure determining routine. More specifically described, the control device determines respective amplitudes of respective heartbeat-synchronous pulses of the right-brachium pulse wave represented by the right-brachium-pulse-wave signal $SM_R$ continuously supplied from the pulse-wave filter circuit 32, and respective values of the right-brachium cuff pressure $PC_R$, represented by the right-brachium-cuff-pressure signal $SC_R$ continuously supplied from the static-pressure filter circuit 30, at respective times of detection of the respective pulses of the right-brachium pulse wave. Based on the change of the amplitudes and the respective values of the right-brachium cuff pressure $PC_R$, the control device determines a right-brachium systolic blood pressure $BPR_{SYS}$, a right-brachium mean blood pressure $BPR_{MEAN}$, and a right-brachium diastolic blood pressure $BPR_{DIA}$, according to a well-known oscillometric blood-pressure determining algorithm. Similarly, the control device determines left-brachium blood pressure values BPL. More specifically described, the control device determines respective amplitudes of respective heartbeat-synchronous pulses of the left-brachium pulse wave represented by the right-brachium-pulse-wave signal $SM_L$ continuously supplied from the pulse-wave filter circuit 50, and respective values of the left-brachium cuff pressure $PC_L$, rep resented by the left-brachium-cuff-pressure signal $SC_L$ continuously supplied from the static-pressure filter circuit 48, at respective times of detection of the respective pulses of the left-brachium pulse wave. Based on the change of the amplitudes and the respective values of the left-brachium cuff pressure $PC_L$, the control device determines a left-brachium systolic blood pressure $BPL_{SYS}$, a left-brachium mean blood pressure $BPL_{MEAN}$, and a left-brachium diastolic blood pressure $BPL_{DIA}$.

Subsequently, at S5, the control device judges whether the determination of blood-pressure values has been completed. If a negative judgment is made at S, S4 is repeated. Meanwhile, if a positive judgment is made at S5, the control goes to S6 to operate the display device 68 to display the left-brachium blood-pressure values BPL and the right-brachium blood-pressure values BPR, determined at S4, in the left-brachium-blood-pressure display area 86 and the right-brachium-blood-pressure display area 88 of the image screen 68a, respectively.

Then, at S7 the control device operates the pressure control valves 26, 44 so as to release each of the right-brachium cuff pressure $PC_R$ and the left-brachium cuff pressure $PC_L$ to an atmospheric pressure. In FIG. 3, S1 through S3 and S7 correspond to the right-brachium-cuff-pressure changing means 70 and the left-brachium-cuff-pressure changing means 74.

Then, the control goes to S8 corresponding to the left-and-right-superior-limb-blood-pressure-ratio calculating means 78. At S8, the control device calculates a left-and-right-superior-limb blood-pressure ratio BBI between the left-brachium blood-pressure value BPL and the right-brachium blood-pressure value BPR, each determined at S4. The left-brachium blood-pressure value BPL may be any one of the left-brachium systolic, mean, and diastolic blood-pressure values, and the right-brachium blood-pressure value BPR may be any one of the right-brachium systolic, mean, and diastolic blood-pressure values. For example, the left-brachium and right-brachium systolic blood-pressure values $BPL_{SYS}$, $BPR_{SYS}$ may be used. In addition, the higher one of the two systolic blood-pressure values $BPL_{SYS}$, $BPR_{SYS}$ is used as a denominator of the left-and-right-superior-limb blood-pressure ratio BBI; and the lower one of the two systolic blood-pressure values $BPL_{SYS}$, $BPR_{SYS}$ is used as a numerator of the blood-pressure ratio BBI. Then, the control device operates the display device 68 to display the thus calculated left-and-right-superior-limb blood-pressure ratio BBI.

When the display device 68 displays the left-and-right-superior-limb blood-pressure ratio BBI, a person can judge as follows: If the left-and-right-superior-limb blood-pressure ratio BBI is near to 1, the person can understand that the left-rachium systolic blood pressure $BPL_{SYS}$ and the right-brachium systolic blood pressure $BPL_{SYS}$ are near to each other, and judge that neither of the left and right superior-limb arteries would probably have stenosis. On the other hand, if the left-and-right-superior-limb blood-pressure ratio BBI is smaller than a prescribed standard value, e.g., 0.9, the person can understand that either one of the left and right systolic blood pressure $BPL_{SYS}$, $BPL_{SYS}$ is considerably lower than the other systolic blood pressure, and judge that the blood pressure would be low because there would be arteriostenosis in a body portion on an upstream side of a left or right body portion where blood pressure values are measured.

Thus, the above-described arteriostenosis inspecting apparatus 10 utilizes the fact that if one of the left and right superior-limb arteries of the subject has stenosis, then the systolic blood pressure in the one artery lowers. Therefore, the left-and-right-superior-limb blood-pressure ratio BBI determined by the left-and-right-superior-limb-blood-pressure-ratio determining means 78 (S8) in the case where neither of the left and right superior-limb arteries has stenosis is near to 1, whereas the ratio BBI determined in the case where either of the two superior-limb arteries has stenosis is significantly smaller, or significantly greater, than 1. Thus, based on the left-and-right-superior-limb blood-pressure ratio BBI determined by the left-and-right-superior-limb-blood-pressure-ratio determining means 78 (S8), a person such as a doctor can diagnose presence or absence of arteriostenosis of a superior-limb artery such as a subclavian artery.

In addition, in the above-described arteriostenosis inspecting apparatus 10, the left-and-right-superior-limb-blood-pressure-ratio determining means 78 (S8) determines the left-and-right-superior-limb blood-pressure ratio BBI by using the lower one of the left-brachium systolic blood pressure $BPL_{SYS}$ and the right-brachium systolic blood pressure $BPR_{SYS}$ as a numerator of the ratio BBI, and using the higher one of the two systolic blood pressure $BPL_{SYS}$, $BPR_{SYS}$ as a denominator of the ratio BBI. Therefore, the presence of arteriostenosis always results in lowering the left-and-right-superior-limb blood-pressure ratio BBI. Thus, when the subject suffers arteriostenosis, the left-and-right-superior-limb blood-pressure ratio BBI changes in the same manner as the ankle-and-brachium blood-pressure index as another index useful in diagnosing arteriostenosis. Therefore, misdiagnoses can be reduced.

While the present invention has been described in detail in its embodiment by reference to the drawings, it is to be understood that the invention may otherwise be embodied.

For example, in the above-described arteriostenosis inspecting apparatus 10, the left-and-right-superior-limb blood-pressure ratio BBI is determined such that the lower one of the left and right systolic blood-pressure values $BPL_{SYS}$, $BPR_{SYS}$ is used as the numerator of the blood-pressure ratio BBI; and the higher one of the two systolic blood-pressure values $BPL_{SYS}$, $BPR_{SYS}$ is used as the denominator of the same BBI. However, a pre-selected one of the two sorts of systolic blood-pressure values $BPL_{SYS}$, $BPR_{SYS}$ may be used as the denominator of the blood-pressure ratio BBI. For example, in the case where each left-brachium systolic blood-pressure value $BPL_{SYS}$ is used as the denominator of blood-pressure ratio BBI, if the left superior-limb artery has stenosis and accordingly the left-brachium systolic blood pressure $BPL_{SYS}$ lowers, then the blood-pressure ratio BBI may be significantly greater than 1. Contrarily, if the right superior-limb artery has stenosis and accordingly the right-brachium systolic blood pressure $BPR_{SYS}$ lowers, then the blood-pressure ratio BBI may be significantly smaller than 1. Thus, the person can judge which one of the left and right superior limbs has arteriostenosis, depending on whether the blood-pressure ratio BBI is greater or smaller than 1.

In addition, in the above-described arteriostenosis inspecting apparatus 10, the display device 68 displays the left-and-right-superior-limb blood-pressure ratio BBI itself. However, it is possible to calculate a difference between the ratio BBI and 1 and display the difference on the display device 68. In this case, a person can judge presence or absence of arteriostenosis based on how far the value displayed by the display device 68 is from 0.

In addition, in the above-described arteriostenosis inspecting apparatus 10, the blood-pressure values are measured from the brachia 12, 16 of the subject. However, blood-pressure values may be measured from wrists of a living subject.

In addition, in the above-described arteriostenosis inspecting apparatus 10, the blood-pressure values are measured using the cuffs 20, 40 worn on the brachia 12, 16 by the oscillometric method. However, blood-pressure values may be measured by so-called K-sound method in which blood-pressure values are determined based on respective values of cuff pressure at respective times when Korotkoff sounds are first and last detected. Otherwise, blood-pressure values may be measured by a supersonic Doppler method in which supersonic-wave oscillator and receiver, placed right above an artery, detect opening and closing of the arterial vessel during changing of cuff pressure. Moreover, blood-pressure values may be measured without using a cuff, for example, by an invasive method in which blood-pressure values are measured using a catheter inserted in an artery, or by a tonometric method in which a pressure pulse wave is detected by pressing an appropriate artery, such as radial artery, via skin and blood-pressure values are determined based on magnitudes of the pressure pulse wave.

It is to be understood that the present invention may be embodied with other changes, improvements and modifications that may occur to a person skilled in the art without departing from the spirit and scope of the invention defined in the appended claims.

What is claimed is:

1. An arteriostenosis inspecting apparatus, comprising:
   a left-superior-limb-blood-pressure measuring device which measures a left-superior-limb blood pressure of a left superior limb of a living subject;
   a right-superior-limb-blood-pressure measuring device which measures a right-superior-limb blood pressure of a right superior limb of the subject; and
   a left-and-right-superior-limb-blood-pressure-ratio determining means for determining a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device.

2. An arteriostenosis inspecting apparatus, comprising:
   a left-superior-limb-blood-pressure measuring device which measures a left-superior-limb blood pressure of a left superior limb of a living subject;
   a right-superior-limb-blood-pressure measuring device which measures a right-superior-limb blood pressure of a right superior limb of the subject; and
   a left-and-right-superior-limb-blood-pressure-ratio determining means for determining a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device,
   wherein the left-and-right-superior-limb-blood-pressure-ratio determining means determines the left-and-right-superior-limb blood-pressure ratio by using a lower one of the left-superior-limb blood pressure and the right-superior-limb blood pressure as a numerator of said ratio and using a higher one of the left-superior-limb blood pressure and the right-superior-limb blood pressure as a denominator of said ratio.

3. An arteriostenosis inspecting apparatus, comprising:
   a left-superior-limb-blood-pressure measuring device which measures a left-superior-limb blood pressure of a left superior limb of a living subject;
   a right-superior-limb-blood-pressure measuring device which measures a right-superior-limb blood pressure of a right superior limb of the subject; and
   a left-and-right-superior-limb-blood-pressure-ratio determining means for determining a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device,
   wherein the left-and-right-superior-limb-blood-pressure-ratio determining means determines the left-and-right-superior-limb blood-pressure ratio by using a preselected one of the left-superior-limb blood pressure and the right-superior-limb blood pressure as a denominator of said ratio.

4. An arteriostenosis inspecting apparatus according to claim 1, further comprising a display device which displays the left-and-right-superior-limb blood-pressure ratio determined by the left-and-right-superior-limb-blood-pressure-ratio determining means.

5. An arteriosclerosis evaluating apparatus according to claim 4, wherein the display device further displays the left-superior-limb blood pressure measured by the left-superior-limb-blood-pressure measuring device, and the right-superior-limb blood pressure measured by the right-superior-limb-blood-pressure measuring device.

6. An arteriostenosis inspecting apparatus, comprising:
   a left-superior-limb-blood-pressure measuring device which measures a left-superior-limb blood pressure of a left superior limb of a living subject;
   a right-superior-limb-blood-pressure measuring device which measures a right-superior-limb blood pressure of a right superior limb of the subject; and
   a left-and-right-superior-limb-blood-pressure-ratio determining device which determines a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device.

* * * * *